US005798265A

United States Patent [19]
Springer et al.

[11] Patent Number: 5,798,265
[45] Date of Patent: Aug. 25, 1998

[54] PSEUDORABIES VIRUS (PRV) POLYNUCLEOTIDES AND THEIR USE FOR PREPARING VIRUS-RESISTANT EUKARYOTIC CELLS

[75] Inventors: Wolfgang Springer; Jörg Baumgarten, both of Wuppertal; Axel Kretschmer, Bergisch Gladbach; Heinz Kölbl, Cologne; Antonius Löbberding, Wuppertal; Walter Strube, Cologne; Peter Thein, Oberzeitlbach, all of Germany

[73] Assignee: Bayer Aktiengesellschaft, Leverkusen, Germany

[21] Appl. No.: 343,281

[22] Filed: Nov. 22, 1994

Related U.S. Application Data

[63] Continuation of Ser. No. 29,202, Mar. 10, 1993, abandoned.

[30] Foreign Application Priority Data

Mar. 13, 1992 [DE] Germany .......................... 42 08 107.6

[51] Int. Cl.$^6$ ............................ C12N 5/10; C12N 15/86; C07H 21/02; C07H 21/04

[52] U.S. Cl. ....................... 435/364; 435/325; 435/320.1; 536/24.5

[58] Field of Search .............................. 435/240.2, 320.1, 435/91.1, 69.1, 172.1, 172.3, 325, 364, 363; 536/23.1, 24.1, 24.5

[56] References Cited

U.S. PATENT DOCUMENTS 5,190,931 3/1993 Inouye et al. ............................ 435/91

OTHER PUBLICATIONS

S. Kit et al. (1986), *Am.J. Vet. Res.*, 46, 1359–1367.
G. Wittmann et al., 1989, "Anjeszky's Disease (Pseudorabies) in Pigs," in *Herpes virus Disease of Cattle, Horses and Pigs*, G. Wittman (Editor), Kluwer Academic Publishers.

G. Wittmann, H.–J. Rziha: Aujezsky's Disease (Pseudorabies) in Pigs, Federal Research Centre for Virus Diseases of Animals, Tübingen.

A.K. Robbins et al.: The Pseudorabies Virus gII Gene is closely related to the gB Glycoprotein Gene of Herpes Simplex Virus in: Journal of Virology, Sep. 1987, pp. 2691–2701.

H. Weintraub et al., Anti–sense RNA as a molecular tool for genetic analysis in: Reviews 1985, pp. 22–25.

K.M.Takayama, M.Inouye: Antisense RNA in: Biochemistry and Molecular Biology 1990, pp. 155–184.

P.J.Green, O.Pines, M.Inouye, The Role of Antisense RNA in Gene Regulattion in: Ann.Rev.Biochem. 1986, pp. 569–597.

B.C.Froehler, Deoynucleoside H–Phosphonate Diester Intermediates in the Synthesis of Internucleotide Phosphate Analogues in: Tetrahedron Letters, vol. 27, 1986, pp. 5575–5578.

S.L.Beaucage, H.M.Caruthers, Deoxynucleoside Phosphoramidites—a new class of key intermediates for deoxypolynucleotides synthesis in: Tetrahedron Letters, vol. 22 1981, pp. 1859–1861.

A.Jäger, J.Engels, Synthesis of Deoxynucleoside Methylphosphonates via a Phosphonamidite Approach in: Tetrahedron Letters, vol. 25 1984, pp. 1437–1440.

W.J.Stec et al., Automated Solid–Phase Synthesis, Separation and Stereochemistry of Phosphorothiosate Analogues of Oligodeoxyribonucleotides in: J.Am.Chem.Soc. 1984, 106, pp. 6077–6079.

J.C.Hanvey et al., Antisense and Antigene Properties of Peptide Nucleic Acids in: Science, vol. 258, 1992, pp. 1481–1485.

Wahl, Stern, Stark in: Proc.Natl.Acad.Sci., USA 76:3683, 1979.

*Primary Examiner*—David Guzo

*Attorney, Agent, or Firm*—Sprung Kramer Schaefer & Briscoe

[57] ABSTRACT

The invention relates to polynucleotides which contain pseudorabies virus sequences, in particular sequences from the gII region of PRV, in the antisense orientation, their preparation and their use.

25 Claims, 4 Drawing Sheets

```
879                                                            938
    GATCACGGACGTGATCGACCGCGCGGGCAAGTGCGTCTCCAAGGCCGAGTACGTGCGCAA
    ----+----+----+----+----+----+----+----+----+----+----+----+
    CTAGTGCCTGCACTAGCTGGCGCGCCCGTTCACGCAGAGGTTCCGGCTCATGCACGCGTT 939                                                            998
    CAACCACAAGGTGACCGCCTTCGACGCGGACGAGAACCCGTCGAGGTGGACCTGCGCCC
    ----+----+----+----+----+----+----+----+----+----+----+----+
    GTTGGTGTTCCACTGGGCGGAAGCTGGCGCTGCTCTTGGGGCAGCTCCACCTGGACGCGGG 999                                                           1058
    CTCGCGCCTGAACGGCTCGGCACCCGGCTGGCACACCACCAACGACACCTACACCAA
    ----+----+----+----+----+----+----+----+----+----+----+----+
    GAGCGCGGACTTGCGCCGAGCCGTGGGCCGACCGTGTGGTGGTTGCTGTGTGGATGTGGTT
```

FIG. 4

PSEUDORABIES VIRUS (PRV) POLYNUCLEOTIDES AND THEIR USE FOR PREPARING VIRUS-RESISTANT EUKARYOTIC CELLS

This application is a continuation of application Ser. No. 08/029,202, filed Mar. 10, 1993, abandoned.

The present invention relates to polynucleotides which contain pseudorabies virus (PRV) sequences, in particular sequences from the gII region of PRV, in the antisense orientation.

To prepare PRV-resistant cells, these polynucleotides are transferred into virus-sensitive cells so that RNA is formed which is complementary to viral mRNAs from PRV and which therefore blocks the synthesis of glycoproteins or other replication proteins that are essential for viral replication.

PRV-resistance in cells and animals is also obtained by antisense oligonucleotides, which are characterized in that they contain gene sequences, especially from the gII region of PRV.

Pseudorabies virus (PRV) is a porcine herpesvirus, which belongs to the alpha-herpesviruses and demonstrates great similarity in structure to the general herpesvirus family. Morphologically it is similar to varicella zoster virus and to equine herpesvirus 1. PRV leads only very occasionally to pathological signs in the immunocompetent adult animal, but in young animals PRV infections have a fatal outcome as a rule. PRV infections are therefore of great economic importance in pig breeding. Moreover, PRV is infectious in many domesticated animals such as cattle, sheep, goats, dogs and cats as well as in many wild animals.

The PRV genome comprises about 145 kbp and codes thereby for about 100 polypeptides. The viral DNA consists of a "unique short" region ($U_s$), which is flanked by inverted-repeat sequences, and a "unique long" region without inverted-repeat sequences. Using Northern blotting it has been possible to detect more than 70 strongly expressed RNA species.

PRV synthesises various glycoproteins, which are present in the viral coat as well as in the cytoplasmic membrane of the infected cells. Additionally, PRV-coded glycoproteins are found which are liberated into the medium. Several of these glycoproteins are clearly bound to each other by means of disulphide bridges. At least 7 PRV glycoproteins have so far been detected on the virus genome.

The surface glycoproteins of herpesviruses play an important part in the infection process, in viral pathogenesis and in the interaction of the virus with the immune system of the host.

Particular protein domains or even complete glycoprotein-coding gene sequences may be conserved in different herpesviruses. For example, it was possible to show that the glycoprotein C and D genes of herpes simplex virus (HSV) possess extensive homology with the PRV G III and PRV GP 50 genes, and that glycoprotein gB of HSV possesses extensive homology with the GII glycoprotein family of PRV. Glycoprotein gB of HSV also possesses substantial homology with certain glycoproteins of Epstein-Barr virus, varicella zoster virus, bovine mammilitis virus and the equine herpesvirus type 1. (G. Wittmann and J. H. Rziha, Herpes virus Disease of cattle, horses and pigs, ed. by G. Wittmann, Developments in veterinary virology, Kluwer Academic Publishers, 1989.)

Antisense-DNA technology has been described by Izant and Weintraub (H. Weintraub, J. G. Izant, R. M. Harland Trends in Genetics, Jan. 1985, 22–25). It is presumed that gene activity is inhibited because an antisense RNA is formed from the integrated polynucleotide that is complementary to the natural mRNA of a particular gene, and an antisense-RNA-mRNA duplex structure therefore arises.

As a result of this, the RNA/RNA duplex structure is degraded very quickly, the nuclear processing and splicing of the mRNA are slowed down considerably, or translation into protein is inhibited. Further possible mechanisms for the antisense inhibition which have been suggested are the blockage of RNA transport through the perinuclear membrane and the blocking of the ribosome/RNA interaction by double-stranded RNA (E. Uhlmann and A. Peyman Chemical Reviews 90, 544–583 (1990)).

The regulation of gene expression by antisense RNA as a naturally occurring mechanism was first detected in prokaryotes. Thus it was shown that interactions of sense RNA transcripts and short antisense RNA transcripts occur in plasmid replication, incompatibility, osmoregulation, transposition and phage reproduction (P. J. Green, O. Pines, M. Inouye Ann. Rev. Biochem. 55, 569–97 (1986)). Naturally occurring antisense genes have also been detected for various eukaryotic systems, such as, for example, the mouse dihydrofolate reductase gene, the Drosophila dopa decarboxylase gene, the heavy chain of the myosin gene of the chicken or the satellite RNA of Cucumber Mosaic Virus (K. M. Tahayama and M. Inouye, Critical Reviews in Biochemistry and Molecular Biology 25, 155 (1990).

The regulation of in vivo gene expression by these antisense transcripts is, however, to a large extent still unclear.

The transient inhibition of the synthesis of gene products by artificial antisense genes was first shown using various antisense oligomers. Problems which arise in this context are the uptake of these oligomers into the cell, nuclease stability and the specific interaction with the target mRNA (E. Uhlmann and A. Peyman, Chemical Reviews, 90, 544–583 (1990).

Besides inhibition by oligomers, artificial inhibition of gene expression was demonstrated by injection of antisense genes/transcripts into Xenopus oocytes and embryos as well as into Drosophila embryos. Integration of antisense genes into the genome of eukaryotic cells has led to the detection of stable inhibition of the gene expression of various genes, such as, for example, of HSV thymidine kinase, of the protooncogenes c-fos, c-myc, c-src, as well as of β-actin genes, of HIV virus genes and also some plant genes, such as, for example, tomato polygalacturonase gene. The activity of antisense genes has also been shown in transgenic organisms.

The present invention relates to:

1. Antisense DNA polynucleotides, which are characterised in that they contain gene sequences of PRV, which are located in the antisense orientation to a promoter sequence.

2. Antisense DNA polynucleotides, which are characterised in that they contain gene sequences from the gII region of PRV, which are located in the antisense orientation to a promoter sequence.

3. Antisense DNA polynucleotides, which are characterised in that they contain a 180 bp-sized region corresponding to the nucleotide sequence 879-1058 of the gII region of PRV, which is located in the antisense orientation to a promoter sequence.

4. Antisense RNA polynucleotides, which are characterised in that they contain gene sequences of PRV.

5. Antisense RNA polynucleotides, which are characterised in that they contain gene sequences from the gII region of PRV.

6. Antisense RNA polynucleotides, which are characterised in that they contain a 180 bp-sized region corresponding to the nucleotide sequence 879-1058 of the gII region of PRV.

7. Antisense oligonucleotides, which are characterised in that they contain gene sequences of PRV, which are complementary to viral RNAs of PRV.

8. Antisense oligonucleotides, which are characterised in that they contain gene sequences from the gII region of PRV, which are complementary to the viral gII RNA of PRV. 9. Antisense oligonucleotides, which are characterised in that they contain gene sequences from a 180 bp-sized region (879-1058) from the gII region of PRV, which are complementary to the viral gII RNA.

10. Expression vector constructs containing polynucleotides from PRV in the antisense orientation to promoter sequences.

11. Expression vector constructs containing polynucleotides from the gII region of PRV in the antisense orientation to promoter sequences.

12. Expression vector constructs containing a 180 bp polynucleotide (879-1058) from the gII region of PRV in the antisense orientation to promoter sequences.

13. Cells and descendants of these cells containing antisense polynucleotides according to points 1 to 6.

14. Pigs which contain in their cells antisense polynucleotides according to points 1 to 6 and 10 to 12.

15. Pigs which contain in their cells antisense oligonucleotides according to points 7 to 9.

16. A method for preparing PRV-resistant cells, characterised in that polynucleotides according to points 1 to 6 or 10 to 12 are transferred into virus-sensitive cells, RNA complementary to the viral RNA is formed and viral replication of PRV is thereby prevented.

17. A method for inhibiting PRV infections, characterised in that antisense oligonucleotides according to points 7 to 9 are administered to animals.

18. Use of polynucleotides according to points 1 to 6 or 10 to 12 for transfer into cells which are suitable for the production of transgenic PRV-resistant animals.

The terms used above have the following meaning: Antisense DNA polynucleotides are relatively small natural or synthetic nucleic acid polymers which may contain from a minimum of 10-20 nucleotide bases up to several thousand nucleotide bases. These polynucleotides are transferred into cells which are sensitive to PRV viruses. That process is termed transformation in which the genotype of a recipient cell is altered by the introduction of e.g. antisense polynucleotides. Those polynucleotides are termed antisense DNA polynucleotides which contain single-stranded or double-stranded DNA molecules, in which the coding strand can be transcribed in the 3'---5' direction so that antisense RNA is formed which is complementary to the virus mRNA. As a result of the formation of the RNA/RNA-duplex structure, viral protein synthesis can no longer take place. For the transcription of antisense RNA, the antisense DNA polynucleotide contains transcription signals, so-called promoter sequences, e.g. of the SV40 promoter, prior to the PRV gene fragment present in the antisense orientation. By selecting certain regions from the PRV genome, such as, for example, from the gII region of PRV, or parts of the gII region, antisense polynucleotides can be constructed which are particularly effective in inhibiting PRV virus synthesis.

Antisense RNA polynucleotides are single-stranded RNA molecules with a length of a few hundred to several thousand nucleotide bases, which are complementary to a region of the viral RNA and thereby can inhibit the translation of the viral mRNA. In contrast to antisense DNA polynucleotides, antisense RNA polynucleotides cannot be stably integrated into the genome of recipient cells.

Antisense oligonucleotides are single-stranded DNA molecules which contain from 10-20 nucleotide bases up to 100 nucleotide bases. Besides the natural nuclease-sensitive oligonucleotide diester molecules, this category includes nuclease-resistant oligonucleotide derivatives such as, for example, methylphosphonate oligonucleotides, phosphorothioate oligonucleotides, peptide nucleid acids (S. J. C. Hanveg et al. Science 258, 1481 (1992)) or other pseudooligonucleotides.

5' amidate oligonucleotides. The sequence of these oligonucleotides is complementary to particular regions of the viral RNA.

To achieve the antiviral effect, the oligonucleotides must be taken up using the natural uptake mechanisms of the cell. To produce PRV resistance in an animal, the oligonucleotides must be administered to the animal using suitable methods.

Suitable antisense vector constructs are eukaryotic expression vectors which contain the PRV DNA in the antisense orientation to promoters. Such vectors as a rule possess regions, so-called replicons, which permit replication in prokaryotes (e.g. pMB1) or eukaryotes (e.g. SV40). Additionally, transcription signals, so-called promoter sequences, are present, which permit the transcription of antisense DNA inserted behind them. Such promoter sequences are, e.g., the early or late SV40 promoter, the thymidine kinase promoter or the metallothionine promoter. As the number of antisense-RNA transcripts rises, so does the probability of producing improved antisense inhibition activity as the result of increased export from the nucleus or greater accumulation in the cytoplasm.

In order to produce a highly stable mRNA, termination of the antisense-RNA transcript is effected with the polyadenylation signal from, e.g., SV40 or bovine growth hormone. In addition, in order to be able to select cells which following transfection contain the gene construct for the antisense-RNA expression, the vectors contain genes for expressing selection markers in prokaryotes, e.g. ampicillin resistance and eukaryotes e.g. neomycin or G418. This selection marker has shown to be effective in animal cells which are PRV-sensitive. Other selection markers may also be used, such as, for example, puromycin, hygromycin or methotrexate in combination with transfection of the gene for dihydrofolate reductase.

Virus-sensitive cells are embryonic chicken fibroblasts, primary kidney cells from rabbit, horse, cattle, dog, cat, monkey or hamster, Vero cells, BHK cells, ED cells and HeLa cells.

Virus-sensitive cells of the pig are, in particular, the cells of the whole upper and lower respiratory tract and of the nasal mucosa and the lung tissue, as well as regional lymph nodes, such as for example, tonsils, and cells of the brain and other nerve tissue, as well as blood cells and cells of the uterine and fetal tissues.

Any strains of PRV can be employed for preparing the antisense-DNA polynucleotides according to the invention.

Such strains are obtained from infected animals in a manner known per se and replicated in a manner known per se in virus-sensitive cells in the usual replication media. Following isolation of the PRV nucleic acid, normal recombinant DNA methods, as described, e.g., in Example 1, are used to prepare E.coli clones which harbour PRV gene fragments in the antisense orientation to a eukaryotic promoter in an expression vector. These PRV gene fragments are replicated in *E.coli* with the aid of the vector, the DNA is isolated in a manner known per se and the PRV DNA together with the promoter and the termination sequences is excised from the vector using restriction enzymes, and isolated, or else the whole vector construct is employed for preparing virus-resistant cells.

Chemical synthesis of antisense oligonucleotides may be carried out on the basis of the published sequence for PRV (Robbis et al., J.Virology, 61, 2692–2701, 1987) using the amidite method of S. L. Beaucage and M. H. Caruthers, Tetrahedron Letters 22, 1859–1862 (1981).

Oligonucleotide derivatives, such as methylphosphonates or phosphorothioates may be prepared by published methods (W. J. Stec et al., J.Am.Chem.Soc. 106, 6077, 1984; B. C. Froehler, Tetrahedron Letters 27, 5575, 1986; A. Jäger, J. Engels, Tetrahedron Letters 25, 1437, 1984).

Antisense-RNA polynucleotides may be prepared using normal recombinant DNA methods. For this purpose, PRV gene fragments, in particular from the gII region, are cloned in vectors in the antisense orientation to strong RNA polymerase promoters such as SP6, T3 and T7, and antisense RNA prepared with commercially available in vitro transcription systems.

For example, the effect on viral gene replication of different antisense-DNA fragments from the region of the gII glycoprotein gene of PRV is described in the present invention.

For this purpose, the gII gene from PRV was cloned from an *E.coli* plasmid into a prokaryotic-eukaryotic vector using normal recombinant DNA methods, so that the gII gene was present in the sense and antisense orientation to the SV40 promoter of the vector (G. Wittman and H. J. Rziha, Herpes Virus Disease of Cattle, horses and pigs, ed, by G. Wittman, Developments in veterinary virology Kluwer Academie Publishers, 1989). In principle, in order to achieve antisense RNA expression, use can also be made of other promoter sequence elements or hybrids of two different promoter sequence elements, which can be expected to elicit strong expression of the antisense RNA in the target cells. In order to optimise RNA-processing, transport and stability, different termination sequences, as well, can be used for terminating and polyadenylating the antisense RNA. Examples are given here for the SV40 early promoter sequence and the SV40 small t antigen termination sequence.

As well as virtually the whole of the gII gene, DNA fragments of 0.1 to 1.5 kb in size were also cloned into the pBEH vector in a similar manner. The sense or antisense orientation of the PRV gII fragments was examined by sequencing these constructs.

Using cell-biological techniques, these PRV gII antisense constructs were transfected into cells which were sensitive to PRV viruses. Clones harbouring the antisense constructs were isolated by means of the G418 resistance of cotransfected, neomycin-resistant constructs.

The inhibition test with pseudorabies viruses was used to determine whether clones had arisen which were resistant to virus infections or virus replication because of the expressed PRV gII-antisense RNA.

This revealed, for example, that strong inhibition of PRV virus replication was obtained with a 180 bp-long antisense construct corresponding to nucleotides 879 to 1058 of the gII region of PRV.

Demonstration of the fact that these virus-resistant cell clones did indeed harbour antisense-DNA constructs was performed using a DNA hybridization technique, the so-called Southern blot technique, in association with the polymerase chain reaction (PCR). The expression of antisense RNA in the virus-resistant cell clones was examined by the Northern blot hybridization technique.

The present invention relates preferably to antisense DNA polynucleotides, which are characterised in that they contain gene sequences of PRV gene sequences from the gII region of PRV, or a 180 bp-sized region corresponding to the nucleotide sequence 879-1058 of the gII region of PRV, which are located in the antisense orientation to a promoter sequence.

The present invention preferably relates to antisense RNA polynucleotides, which are characterised in that they contain gene sequences of PRV, of the gII region of PRV or of a 180 bp-sized region corresponding to the nucleotide sequence 879-1058 of the gII region of PRV in the antisense orientation.

Amongst these are also preferably antisense oligonucleotides which are characterised in that they contain gene sequences from PRV, the gII region of PRV or a 180 bp-sized region (879-1058) from the gII region of PRV, which are complementary to the viral PRV RNA.

The invention also preferably comprises expression vector constructs, which contain, in the antisense orientation to promoter sequences, polynucleotides from PRV, from the gII region of PRV or from a 180 bp polynucleotide (879-1058) from the gII region of PRV, as well as cells and descendants of these cells, and also animals which contain these antisense polynucleotides or expression vector constructs.

The invention also relates to processes for preparing PRV-resistant cells, characterised in that antisense polynucleotides and also expression vector constructs with antisense polynucleotides are transferred into virus-sensitive cells and that RNA complementary to the viral RNA is formed and that viral multiplication of PRV is thereby prevented. Among these are processes for inhibiting PRV infections, characterised in that antisense oligonucleotides are administered to animals. The invention also relates to the use of antisense polynucleotides for transfer into cells which are suitable for producing transgenic, PRV-resistant animals.

EXAMPLES

Example 1

Recombinant-DNA preparation of PRV antisense-DNA constructs

Isolation of PRV gII DNA

The starting point for the isolation of the gII glycoprotein gene of PRV was the clone PRV1A, which was provided by the Bundesforschungsanstalt für Viruskrankheiten der Tiere (Federal Research Institute for Viral Diseases of Animals), T übingen.

The recombinant plasmid with the gII sequence was isolated in preparative quantities from the *E.coli* clone PRV1A. For this purpose 500 ml of an overnight culture in LB medium containing ampicillin (50 mg/i) were centrifuged at 4,000 rpm for 10 minutes at 40° C. in a refrigerated centrifuge, and the cell sediment was suspended in 10 ml of lysozyme mix (9 ml of 25% sucrose in 50 mM Tris/HCl pH 7.5 and 1 ml of 10 mg/ml lysozyme). The cells were incubated at room temperature for at least 30 minutes. 2 ml of 500 mM EDTA pH 8 and 15 ml of Triton mix (5 ml of Triton, 62.5 ml of 500 mM EDTA, 25 ml of 1M Tris/HCl pH 8, 33.75 ml/$H_2O$) were then added and the mixture shaken until only one homogeneous phase was to be seen.

The samples were placed in ice for 30 minutes and then centrifuged for 1 hour at 13,000 rpm in the refrigerated centrifuge (JA 17 rotor, Beckmann). The supernatant was transferred to ultracentrifuge tubes (28 g of CsCl, 30 g of nucleic acid supernatant, 4 ml of ethidium bromide (10 ml/ml)). The tubes were sealed and centrifuged in the Ti⁵O rotor for at least 14 hours at 45,000 rpm and 20° C. Following centrifugation, the lower plasmid band was isolated under UV light using a syringe and the ethidium bromide was removed by repeated extraction with CsCl-saturated isopropyl alcohol.

The caesium chloride was removed from the DNA solution by dialysing for 3 hours against TE buffer, with hourly buffer changes.

LB medium contains 10 g of Bacto tryptone, 5 g of yeast extract, 10 g of NaCl 1 l of $H_2O$, pH 7.5. TE buffer contains 10 mM Tris/HCl, pH 8.0, 1 mM EDTA.

Cloning of the gII DNA in eukaryotic expression vectors

The recombinant plasmid from clone PRV1A, containing the gII sequence, was cleaved with the restriction sequences Sph I, and the 2.9 kB-sized Sph gII fragment was isolated by preparative agarose gel electrophoresis and electroelution with the Electroelutor from International Bio-technologies Inc., New Haven.

The 2.9 kb-sized Sph I gII fragment was firstly cloned into the SpH I site of the vector pUC 19 (Pharmacia, Uppsala, Sweden) using standard recombinant DNA methods (Maniatis et al., Molecular Cloning, Cold Spring Harbor Laboratory Press, 1989). The recombinant pUC 19 plasmid with the SpH I gII fragment was isolated from a corresponding pUC 19 clone, and the gII fragment was excised from the polylinker region of pUC 19 with the restriction enzymes EcoRI and Hind III and isolated by agarose gel electrophoresis and electroelution.

The 2.9 kb-sized EcoRI/Hind III gII fragment was employed for further cloning in eukaryotic expression vectors either directly or following cleavage with the restriction enzyme Sau III A.

The eukaryotic expression vector pBEH, which was provided by the GBF Braunschweig, was used for cloning the 2.9 kb-sized EcoRI/Hind III gII fragment and the SauIII fragments of PRV. The cloning strategy was chosen so that the EcoRI/HindIII gII fragment is expressed from the SV40 early promoter in the antisense orientation. The SauIII A fragments of the gII region were cloned into the BamHI site of the polylinker of pBEH in the sense and antisense orientation. The DNA constructs were transformed into E.coli by electroporation.

For the electroporation, electro-competent E.coli cells were first prepared. 500 ml of E.coli culture solution at an OD of 0.5 (550 nm) were centrifuged at 4000 g. The cells were washed in an equal volume of ice-cold, sterile, double-distilled $H_2O$. The washing was repeated twice. Subsequently the cells were washed with 50 ml of cold 10% glycerol/double-distilled $H_2O$, centrifuged at 5000 rpm and then taken up in 1–5 ml of 10% strength glycerol/double-distilled $H_2O$. The cells were stored at −70° C.

The electroporation (EP) was carried out using the Gene Pulser Apparatus and Capacitance Extender from BioRad.

50 ml of cells were thawed on ice and transferred to a 0.2 cm EP cuvette, and 10–50 ng of DNA in 5–10 µl of double-distilled $H_2O$ were added.

The EP conditions were:

Capacitance: 250 uF

Voltage: 2.5 kv

Resistance: 200 ohm

G. Pulser: 25 uF

Electrode gap: 0.2 cm

According to the EP, the pulse should be 4–5 msec. 1 ml of SOC medium (2% of Bacto tryptone, 0.5% of Bacto yeast extract, 10 mM NaCl, 2.5 mM KCl, 10 mM $MgCl_2$, 10 MM $MgSO_4$ and 20 mM glucose) were added immediately after pulsing and the cuvette contents transferred to a sterile tube. After interim culturing at 37° C. for 1 hour, the contents were plated out. E.coli clones expressing the ampicillin resistance of the pBEH vector were characterised using molecular biological techniques.

Molecular characterisation of the PRV expression constructs in E.coli

For the molecular biological characterisation of the pBEH-containing clones, the plasmids were isolated using standard analytical procedures for isolating nucleic acids.

Agarose gel electrophoresis was used to identify those clones which had the EcoRI/HindIII gII fragment or SauIIIA gII fragments inserted into the pBEH vector.

To demonstrate the sense or antisense orientation of the SauIII A gII fragments in the pBEH vector, the SauIII A gII fragments were sequenced by the Sanger method using SV40 primers and a Sequenase kit from USB, Cleveland, Ohio, and the orientation determined by comparison with the previously-published sequence of the gII region.

The SauIII A fragments present in the gII sequence are listed in Table 1 below. As examples of the different cloned and tested sense and antisense PRV fragments, 5 antisense constructs are listed which were characterised by insert size, nucleotide region and antisense orientation.

Figure 1:
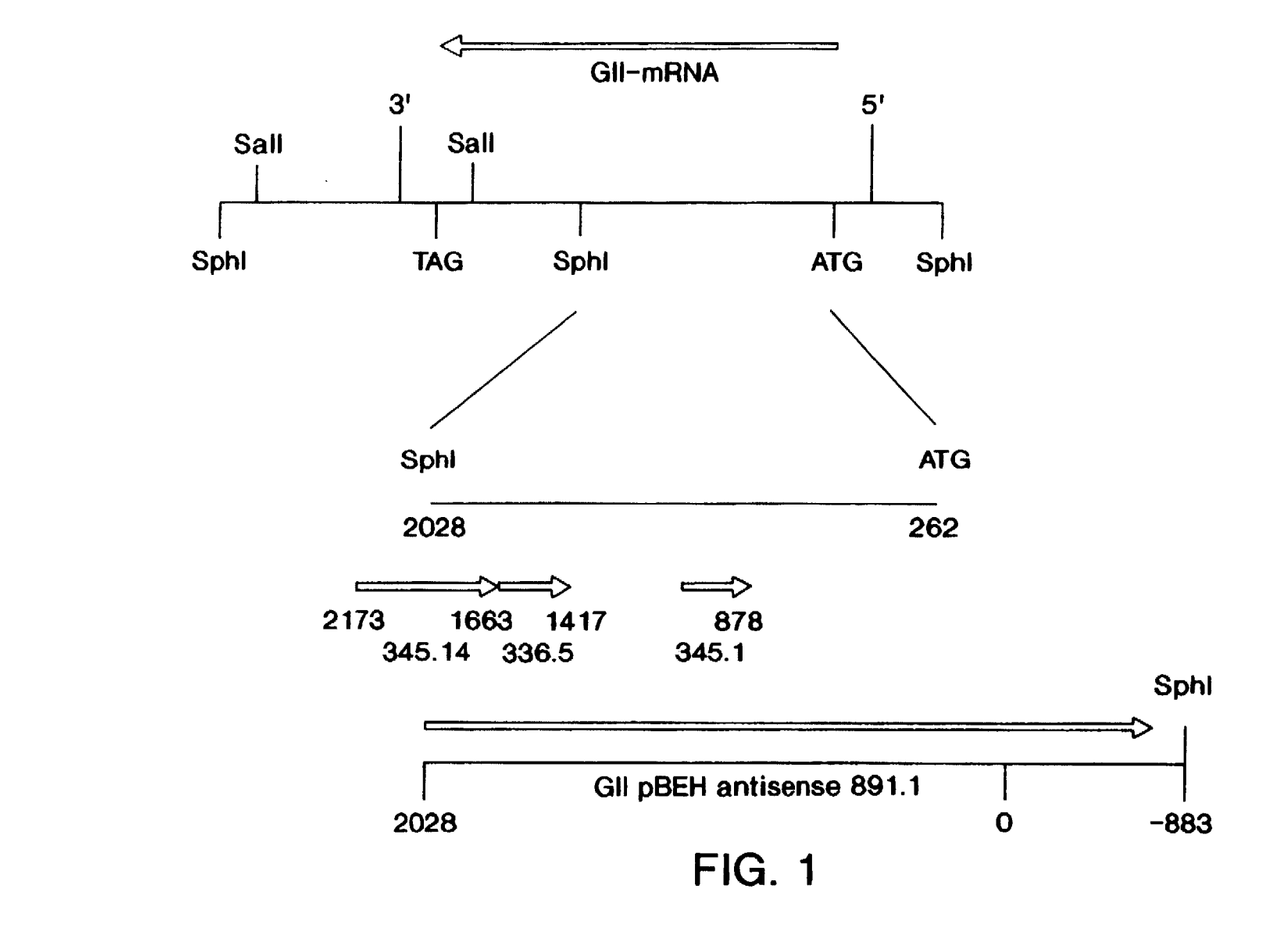
FIG. 1 shows a section of the restriction map of PRV including the gII region of PRV and the location of antisense constructs cited as examples.
Figure 2:
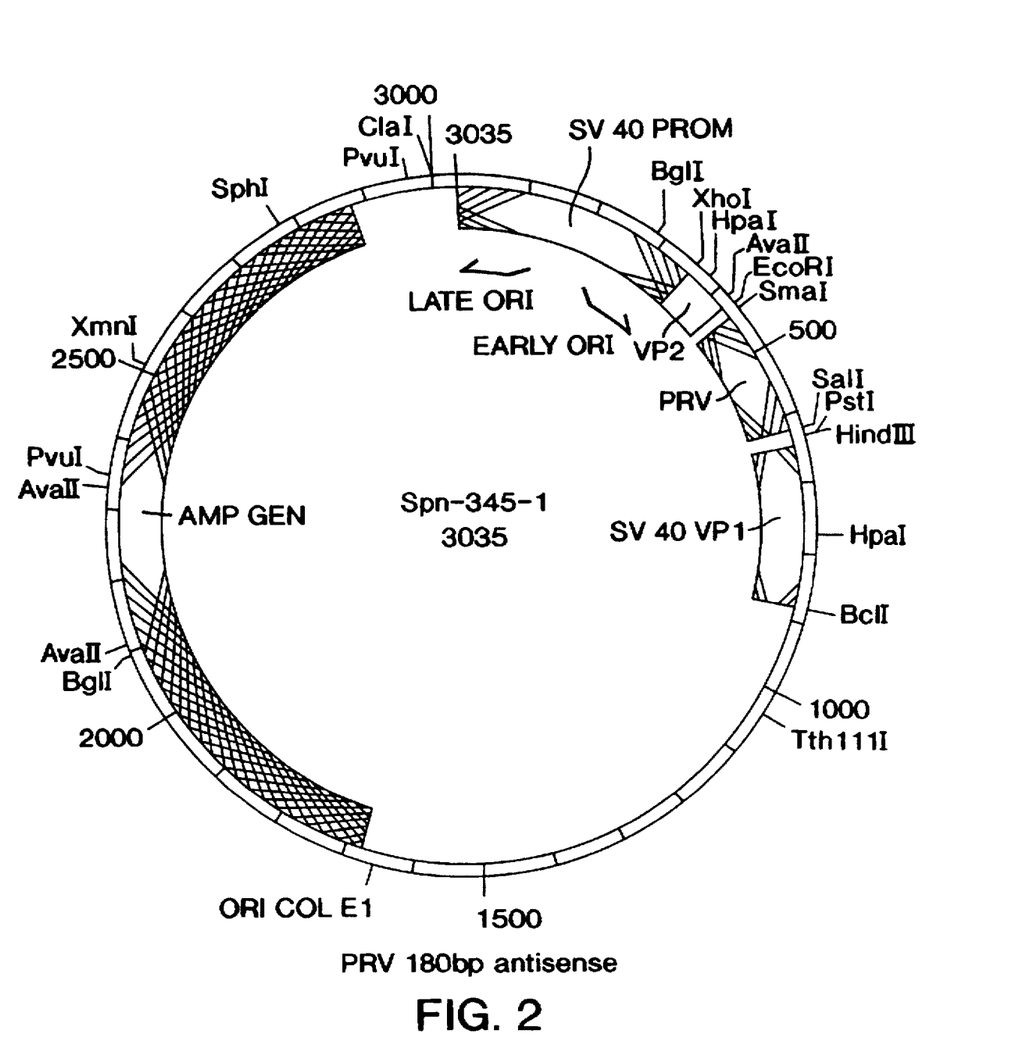
FIG. 2 shows the vector map of pBEH with the 180 bp-long PRV-gII fragment (sequence extent 879-1058) in the antisense orientation to the SV40 early promoter of the vector.
Figure 3:
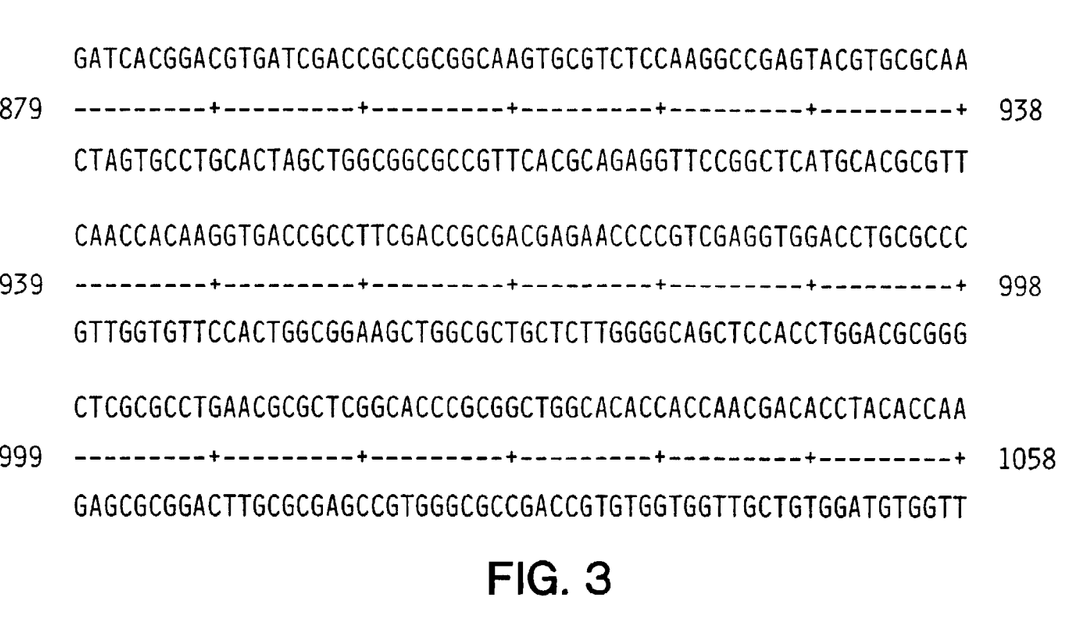
FIG. 3 shows the nucleotide sequence of the 180 bp-long DNA fragment (SEQ ID NO:20) from the gII region of PRV (sequence extent 879-1058), which, in the antisense orientation to a promoter of a eukaryotic expression vector, generates high resistance to PRV in eukaryotic cells.

A portion of the restriction map of PRV, including the gII region, is shown in figure FIG. 1 and the location of the antisense constructs cited as examples is indicated. Figure FIG. 2 shows a restriction map of the vector construct SPN 345-1 which consists of the vector pBEH and a 180 bp-sized Sau III A fragment (nucleotide region 879-1058), which is integrated in the antisense orientation to the SV40 promoter of the vector. Figure FIG. 3 shows the nucleotide sequence of the gII fragment from clone SPN 345.1.

TABLE 1

| Clone designation | Insert size | Extent of gII region | Orientation |
| --- | --- | --- | --- |
| 336-5 | 250 bp | 1417–1653 | antisense |
| 345-1 | 180 bp | 870–1058 | antisense |
| 345-14 (351-4) | 510 bp | 1662–2172 | antisense |
| 345-39 | 600 bp | 1059–1662 | antisense |
| 891-1 | 2900 bp | −883 to 2028 | antisense |

| SauIIIA fragments in PRVG2222 and PRV gII | | | |
| --- | --- | --- | --- |
| Extent | Fragment size | Extent | Fragment size |
| 0–217 | 217 | 1417–1663 | 246 |
| 217–527 | 310 | 1663–2173 | 510 |
| 527–728 | 201 | 2173–2329 | 159 |
| 728–881 | 153 | 2329–2443 | 114 |
| 881–893 | 12 | 2443–2611 | 168 |
| 879–1058 | 180 | 2611–2845 | 234 |
| 1059–1417 | 358 | 2845–3048 | 203 |
| 1059–1663 | 604 | | |

| SphI fragments in PRVG222 | |
| --- | --- |
| Extent | Fragment size |
| 0–2033 | 2033 |
| 2033–3048 | 1015 |

Example 2

Transfection and cloning of Vero cells with PRV antisense-RNA expression vectors Adherently growing Vero cells were chosen as examples of transfected animal cells which show virus resistance against PRV due to endogenously expressed antisense RNA. The cell line was obtained from the American Type Culture Collection (ATCC), 12301 Parklawn Drive, Rockville, Md. 20852-1776, USA.

The cell line was cultured in Medium 199 (from Flow) containing 5% FCS (fetal calf serum), 7.5 ml of penicillin/ streptomycin (10 mg/ml) 5 ml of L-glutamine and 5 ml of non-essential amino acids (Eagle (1959) Science 1343). Vector transfection was carried out using the calcium phosphate method, which gave the best results:

Calcium phosphate method

Variant of the method of Wingler et. al., 1977, Cell 11, 223

The transfection is carried out with Ca precipitates of the DNA. Quantities of DNA varying from 0.05 to 20 µg were dissolved in 0.25 ml of 250 mM $CaCl_2$ and slowly pipetted into 0.25 ml of 2×HEBS buffer. Transfection took place by adding the whole precipitate mixture to 10 ml of cell culture. The medium was aspirated off 15 hours later. After that the cells were shocked with DMSO.

3 ml of a 25% strength solution of DMSO in sterile PBS were used for a 10 ml culture. After 4 min, the supernatant was aspirated off and the cells were washed with 5 ml of PBS. Subsequently the cells were taken up in 10 ml of DMEM medium.

HEBS buffer contains 50 mmol HEPES (N-2-hydroxyethylpiperazine-N'-2-ethane,280 mmol NaCl sulphonic acid sodium salt)

PBS (phosphate-buffered saline) contains in g/liter: KCl 2; $KH_2PO_4$ 2; NaCl 80; $Na_2HPO_4.7H_2O$ 21.6;

DMEM medium (Dulbecco modification of Eagle medium) contains in mg/liter: L-arginine 84; L-cystine 56.78; L-glutamine 584; glycine 30; L-histidine 42; L-isoleucine 104.8; L-leucine 104.8; L-lysine 146.2; L-methionine 30; L-phenylalanine 66; L-serine 42; L-threonine 95.2; L-tryptophan 16; L-tyrosine 89.5; L-valine 93.6; Ca D-pantothenate 4; choline chloride 4; folic acid 4; inositol 7; nicotinamide 4; pyridoxal HCl 4; riboflavin 0.4; thiamine 4; $CaCl_2.2H_2O$ 264.9; $Fe(NO_3)_3.9H_2O$ 0.1; KCl400; $MgSO_4.7H_2O$ 200; NaCl 6400; $NaHCO_3$ 3700; $NaH_2PO_4.2H_2O$ 141.3; D-glucose 4500; phenol red 15; sodium pyruvate 15;

Selection of transfectants 48 hours after the DMSO shock, the cells were trypsinised and resuspended in selection medium (nutrient solution for Vero cells +0.74 mg/ml Geneticin G418). In doing this, the cells from one culture plate were distributed to 5 plates in all and made up to 10 ml volume with selection medium.

The cells were subsequently incubated at 37° C. in a $CO_2$ incubator, with the medium being changed every 3 days initially. This change of medium was continued until all the non-transfected cells had died, and the transfected cells of colonies were carefully aspirated off with an Eppendorf pipette. The cells were subsequently transferred to 0.2 ml of selection medium and expanded until sufficient cells had grown for testing virus resistance.

Example 3

Demonstration of the integration of antisense-PRV constructs in the genome of eukaryotic cells The G418-resistant Vero clones (designated VK18, VK44, VK66, VK69, VK120 and VK159 in FIG. 4) and the non-transfected Vero cell lines designated (V177 and V210 in FIG. 4) were analysed for integration of the PRV-gII antisense-DNA constructs by the Southern blot technique (L. G. Davis et al., Basis Methods in Molecular Biology, Elsevier, N.Y. (1986)) in combination with the polymerase chain reaction (PCR) (PCR Technology Principles and Application for DNA Amplification, Ed. Henry A. Erlich, M. Stockton Press, New York (1989)). For this purpose, 50 ml cell cultures of the different Vero clones were grown first of all. The cells were centrifuged at 2000 rpm in a Beckmann refrigerated centrifuge using a JA 17 rotor. The cell pellet was subsequently resuspended in 3 ml of Tris/HCl buffer, pH 8 (0.025M Tris/HCl 0.025M EDTA and 0.3M sucrose), and incubated at room temperature for 30 minutes. The cells lyse following addition of 300 µl of 0.5 M EDTA, pH 8.0, and 30 µl of 20% strength sodium dodecyl sulphate. To degrade the RNA, 70 µl of RNase (1 mg/ml) were added to the lysate, which was then incubated at 37° C. for 30 minutes. The lysate was diluted to 20 ml with TE buffer and subsequently treated twice with an equal volume of Tris-saturated phenol. Following centrifugation at 6000 rpm in a Heraeus bench centrifuge, the upper, aqueous DNA-containing phase was extracted twice with ether in order to remove traces of phenol. After addition of isopropanol, the precipitated DNA was centrifuged at 5000 rpm and the pellet washed with 70% ethanol. The DNA precipitate was dried in a Speedvac centrifuge and then dissolved in 1-2 ml of buffer.

For detecting integrated PRV DNA, PRV primers from the 5' and 3' terminal region of the 180 bp PRV fragment (SPN 345.1) were employed in order to achieve specific amplification of the integrated PRV DNA by the PCR method. The PCR reaction mixture employed 2 µg of genomic DNA from the Vero clones, 2 µmol of primer 1 and primer 2, 2.5 units of Taq polymerase from Cetus/Perkin-Elmer and 200 µmol of each dNTPS in a total volume of 100 µl of PCR buffer (50 nM KCl, 10 nM Tris/HCl, pH 8.3, 1.5 nM $MgCl_2$ and 0.01% gelatin). Amplification was carried out in a PCR processor from Cetus/Perkin-Elmer.

The mixtures were subjected initially to melting at 94° C. for 2 minutes and 30 seconds then, in each cycle, the DNA was denatured at 94° C. for 1 min., primer annealing was carried out at 40°–45° C. for 2 minutes and primer extension at 72° C. for 3 minutes. After 35 cycles, a 20-minute extension was finally carried out at 72° C. and the mixtures cooled at 4° C.

The amplified DNA samples were fractionated by 1% agarose gel electrophoresis, and the denatured DNA was transferred by the Southern blot hybridisation technique onto a BA 85 nitrocellulose membrane from Schleicher and Schüll and fixed at 80° C. in a vacuum oven.

The nitrocellulose membrane was sealed in a plastic film, and hybridization was carried out by standard methods (Maniatis).

The 180 bp PRV gII fragment (SPN 345.1), labelled either with digoxigenin-dUTP or $P^{32}$-dCTP, was employed as gene probe.

The Southern blots were evaluated either with digoxigenin antibodies, which were conjugated with alkaline phosphatase, and nitro blue tetrazolium/bromochloroindolyl phosphate according to the Boehringer method, or by autoradiography.

The Southern blot hybridization with the PCR-amplified genomic DNA showed that all the amplified DNA fragments with a length of about 0.2 kb hybridized quite specifically to the 180 bp PRV-gII gene probe, while the non-transfected Vero cell DNA gave no hybridization signal.

Figure 4:
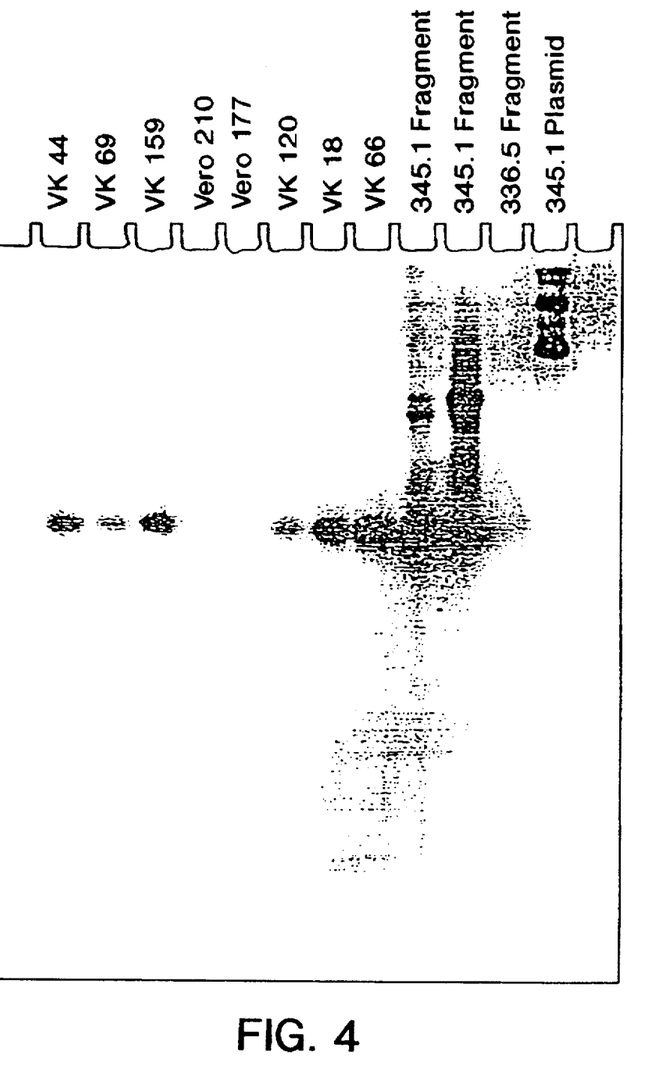
FIG. 4 shows a Southern blot of genomic DNA from the Vero clones VK18, 44, 66, 69, 120 and 159, which are transfected with the SPN 345.1 antisense construct, and from the non-transfected Vero cell lines Vero 177 and 210. The 180 bp fragment 345.1 and the 345.1 plasmid with the 180 bp insert were employed as positive controls. A 250 bp fragment (1417–1663) from gII region was used as negative control.

It was therefore possible to show unambiguously that the antisense PRV DNA is present in the genome of the PRV-resistant Vero clones. The Southern blot/PCR hybridization with the 180 bp PRV gene probe is shown in FIG. 4.

Primer 1 is 5'd(TCACGGACGTGATCGACC)3' (SEQ ID NO:18)

Primer 2 is 5'd(TGTAGGTGTCGTTGGTGGT)3' (SEQ ID NO:19)

dNTPS are deoxynucleoside triphosphates

Example 4

Demonstration of virus resistance of transfected, cloned Vero cell lines

Cloned cell lines which were obtained and characterised according to Examples 1, 2 and 3 were examined for the expression of virus resistance using PRV in comparative infection studies together with the original Vero cell line as control.

Infection of Vero cells, and of Vero clones containing PRV-antisense RNA, with PRV Virus titration for determining the culture-infective dose ($CID_{50}$)

Medium 199 from Flow, with the additions described in Example 2, was used as the nutrient solution for culturing the Vero clones and Vero wild-type cells. 100,000 cells/ml of medium of the wild type and the Vero clones to be tested were sown and incubated at 37° C. for 2–3 days. After that the medium was aspirated off and replaced by virus growth medium (MEME, from Flow+2% FCS). The cells were infected with the original virus culture at a virus dilution of $2 \times 10^{-3}$ to $1 \times 10^{-7}$ and incubated at 37° C. After about 18–20 hours, the incubation was terminated by freezing at –80° C. For determining the $CID_{50}$, BK cells were sown in 96-well microtitre plates at a density of 200,000 cells per ml of nutrient solution and incubated overnight at 37° C. in a $CO_2$ incubator. The medium was MEME +10% FCS. MEME is minimum essential medium Eagle with salts in mg/liter: L-arginine 126.4; L-cystine 28.4; L-glutamine 292.3; L-histidine 41.9; L-isolencine 52.5; L-leucine 52.5; L-lysine 73.06; L-methionine 14.9; L-phenylalanine 33.02; L-threonine 47.64; L-tryptophan 10.2; L-tyrosine 45.02; L-valine 46.9; Ca D-pantothenate 1; choline chloride 1; folic acid 1; inositol 2; nicotinamide 1; pyridoxal/HCl1; riboflavin 0.1; thiamine 1.0; $CaCl_2.2H_2O$ 264.9; KCl 400; $MgSO_4.7H_2O$ 200; NaCl 6800; $NaHCO_3$ 2000; $NaH_2PO_4.2H_2O$ 158.3; D-glucose 1000; phenol red 17;

The virus cultures frozen at –80° C. were thawed and diluted from $10^{-1}$ to $10^{-8}$ in MEME+3% FCS. The medium was then aspirated off from the microtitre plates with the BK cells, and the virus dilutions were added to the BK cells. After 6 days of incubation at 37° C. in a $CO_2$ incubator, the cytopathic effect (CPE) was scored under the microscope.

Microtitre wells in which plaques appeared were taken to be positive.

Plaque test: Determination of infectious units (IU)

Wild-type cells of Vero wild-type cells and Vero clones with integrated PRV-antisense constructs were sown at a density of 100,000 cells per ml in Medium 199+5% FCS and incubated at 37° C. for 2–3 days. Subsequently the medium was exchanged for MEME medium+2% FCS and virus was added at dilutions of $10^{-7}$ and $10^{-8}$. After 60–70 hours, the growth of the viruses was stopped by freezing at –80° C. To determine infectious units, Vero wild-type cells were applied to tissue culture plates (φ5 cm). For this, Vero wild-type was incubated overnight in Medium 199+5% FCS and subsequently infected with the virus incubations from the wild type and the Vero clones at dilutions of $10^{-1}$ and $10^{-7}$. After 3 hours of incubation in a $CO_2$ incubator, methylcellulose medium (MEME+5% FCS+3.75 g of methylcellulose per 500 ml) was added and incubation was continued until plaques were recognisable in the cell culture lawn.

Next, the cells were fixed with a 5% formaldehyde solution and stained with 20% Giemsa solution. The plaques were counted and the number of plaques multiplied by the dilution gave the infectious units (IU).

These tests established that the Vero clones VK18, VK44, VK66, VK69, VK120 and VK159 named in figure FIG. 4, which contain antisense constructs with the 180 bp-long PRV fragment from the gII region, are resistant to PRV, while the Vero wild-type cells and clones with integrated expression vectors lacking a PRV insert possess normal virus sensitivity.

Example 5

Demonstration of PRV antisense-RNA expression in Vero cells

The antisense-RNA expression in the PRV-resistant Vero clones was examined using the Northern blot technique. The cellular RNA was isolated using a standard guanidine isothiocyanate method.

The buffers used were: GII buffer (94.53 g of guanidine isothiocyanate, 1.67 ml of 3M sodium acetate, pH 6, made up to 200 ml with $H_2O$, +1.67 ml of β-mercaptoethanol) and CsCl buffer (95.97 ml of CsCl+0.83 ml of 3M sodium acetate, pH 6, made to 100 ml with $H_2O$, and sterilised by filtration).

The cells were thawed in 8 ml of GII buffer and carefully shaken until they were completely lysed. 4 ml of CsCl buffer were pipetted into SW40 centrifuge tubes and then carefully over-layered with the cell lysate. After 12 hours of centrifugation in the SW40 rotor at 32,000 rpm, the individual phases were pipetted off, the remaining fluid was wiped off the tubes, and the RNA precipitate at the bottom of the tube was then taken up in $2 \times 200$ µl of 0.3M sodium acetate, pH 6, and carefully resuspended. 2.5 volumes of ethanol were next added to the RNA, which was then precipitated at –70° C. for 30 minutes and centrifuged for 10 minutes at 5000 rpm in a bench centrifuge, and the RNA pellet was taken up in 200 µl of 70% strength ethanol and stored at –20° C. Gel electrophoresis of the RNA and Northern blotting were carried as described below.

The following reagents and buffers were used for RNA electrophoresis and Northern blotting:

Reagents:

10×Mops buffer (0.2M 3-morpholinopropanesulphonic acid 0.05M sodium acetate 0.01M EDTA, pH 5.5–7.0)

37% formaldehyde solution

Loading buffer:

0.72 ml of formamide 0.16 ml of 10×Mops 0.26 ml of 37% formaldehyde 0.18 ml of double-distilled $H_2O$ 0.10 ml of 80% glycerol 0.08 ml of Bromophenol Blue saturated in double-distilled $H_2O$ Transfer:

Sterile 10×SSC (1.5M NaCl; 0.15M Na citrate)

Agarose gel:

1 g of agarose 10 ml of 10×Mops 85 ml of double-distilled $H_2O$ dissolved in a microwave and cooled to 50°

+5.5 ml of 37% formaldehyde solution

The gel electrophoresis was carried out for about 1.5 hours in 1×Mops at 193V and 55 mA.

To denature the RNA, the samples precipitated with ethanol were centrifuged at 5000 rpm. The supernatant was poured off and the precipitate was dried at room temperature for about 30 minutes. 20 µl of loading buffer were added by pipette to the samples, which were denatured at 95° C. for 2 minutes and cooled to 4° C. 0.5 µl of ethidium bromide (10 mg/ml) was added to the samples by pipette and the mixtures loaded on the gel. At least 10–15 µg of total RNA were used.

For blotting, the gel was first equilibrated in 10×SSC for 2×15 minutes in order to remove the formaldehyde. The transfer of the RNA onto a pre-treated nitrocellulose membrane (1 min double-distilled $H_2O$ equilibrated with 10×SSC) was effected in an analogous manner to that used in Southern transfer.

For hybridization following the Northern transfer, the nitrocellulose membrane was treated in 30–40 ml of prehybridization buffer (50% formamide, 5×SSC, 50 mM sodium phosphate, pH 6.5, 2.0 µg/ml of sonicated herring sperm DNA, 10×Denhard solution) at 42° C. for 8–20 hours. The prehybridization buffer was discarded and replaced by hybridization buffer (4 parts of prehybridization buffer, 1 part of 50% dextran sulphate solution). The gene probe (10 ng/ml) specific activity $10^8$ cpm/µg) was added and the plastic bag with the nitrocellulose membrane was sealed once more and hybridization took place at 42° C. for 20 hours with gentle shaking.

The membrane was subsequently washed 4 times with 2×SSC+0.1% SDS at 50° C. for 15 minutes, and then wrapped in plastic film and exposed to X-ray film using an enhancement screen.

It was possible, for example, to show in Northern blots of cellular RNA from the virus-resistant Vero clones VK13 and VK18 the presence of antisense-RNA transcripts which hybridised quite specifically with the 180 bp gene probe from SPN 345.1. By contrast, no antisense transcripts were detected in cellular RNA from non-transfected Vero cells.

Example 6
Demonstration of PRV resistance in Vero cells, pretreated with antisense oligonucleotides The biological efficacy of the antisense oligonucleotides of the following sequence listing 28769/1-17, which specifically act on the RNA of the gII gene of PRV, was measured by a virus resistance test. The Vero cells were preincubated for 1 to 3 days in the presence of different concentrations (10 µg-100 µg/ml) of antisense oligonucleotides. The PRV resistance of cells was measured according to example 4.

DESCRIPTION OF THE FIGURES

Figure

Figure

Figure

---

We claim:

1. A DNA molecule selected from the group consisting of:
 (i) DNA encoding RNA that is complementary to mRNA transcribed from nucleotides 879-1058 of the gII region of pseudorabies virus; and
 (ii) a continuous DNA fragment of (i) of about 15 to about 100 nucleotides in length.

2. The DNA according to claim 1, which is DNA encoding RNA that is complementary to mRNA transcribed from nucleotides 879-1058 of the gII region of pseudorabies virus.

3. The DNA according to claim 1, which is a continuous fragment of DNA encoding RNA that is complementary to mRNA transcribed from nucleotides 879-1058 of the gII region of pseudorabies virus, said continuous fragment being about 15 to about 100 nucleotides in length.

4. The DNA according to claim 1, which is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16 and SEQ ID NO:17.

5. The RNA encoded by the DNA according to claim 1.

6. An expression vector comprising the DNA according to claim 1.

7. A Vero cell comprising the DNA according to claim 1.

8. An eucaryotic cell comprising the DNA according to claim 1.

9. The RNA encoded by the DNA according to claim 2.

10. An expression vector comprising the DNA according to claim 2.

11. A Vero cell comprising the DNA according to claim 2.

12. An eucaryotic cell comprising the DNA according to claim 2.

13. The DNA according to claim 3, wherein said continuous fragment is 20 to 100 nucleotides in length.

14. The RNA encoded by the DNA according to claim 3.

15. An expression vector comprising the DNA according to claim 3.

16. A Vero cell comprising the DNA according to claim 3.

17. An eucaryotic cell comprising the DNA according to claim 3.

18. The RNA encoded by the DNA according to claim 13.

19. An expression vector comprising the DNA according to claim 13.

20. A Vero cell comprising the DNA according to claim 13.

21. An eucaryotic cell comprising the DNA according to claim 13.

22. The RNA encoded by the DNA according to claim 4.

23. An expression vector comprising the DNA according to claim 4.

24. A Vero cell comprising the DNA according to claim 4.

25. An eucaryotic cell comprising the DNA according to claim 4.

* * * * *

SEQUENCE LISTING ( 1 ) GENERAL INFORMATION:

( i i i ) NUMBER OF SEQUENCES: 20

( 2 ) INFORMATION FOR SEQ ID NO: 1:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:1:

CCAGCTAGTG CAGGCACTAG        20

( 2 ) INFORMATION FOR SEQ ID NO: 2:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:2:

CCTCTGCGTG AACGGCGCCG        20

( 2 ) INFORMATION FOR SEQ ID NO: 3:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:3:

AACGCGTGCA TGAGCCGGAA                                     20

( 2 ) INFORMATION FOR SEQ ID NO: 4:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:4:

TCCGCCAGTG GAACACCAAC                                     20

( 2 ) INFORMATION FOR SEQ ID NO: 5:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:5:

CCCGCGTCCA GGTGGAGCTG                                     20

( 2 ) INFORMATION FOR SEQ ID NO: 6:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:6:

GCTCGCGCAA GTCCGCGCTC                                     20

( 2 ) INFORMATION FOR SEQ ID NO: 7:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:7:

CCACACGGTC GGCGCCCACG                                     20

( 2 ) INFORMATION FOR SEQ ID NO: 8:

( i ) SEQUENCE CHARACTERISTICS:
        ( A ) LENGTH: 20 base pairs ( B ) TYPE: nucleic acid
        ( C ) STRANDEDNESS: single stranded
        ( D ) TOPOLOGY: linear ( i i ) MOLECULE TYPE: synthetic or biological DNA or RNA ( x i ) SEQUENCE DESCRIPTION: SEQ ID NO:8:

CCCCAAGAGC AGCGCCAGCT 20

( 2 ) INFORMATION FOR SEQ ID NO: 9:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear ( i i ) MOLECULE TYPE: synthetic or biological DNA or RNA ( x i ) SEQUENCE DESCRIPTION: SEQ ID NO:9:

AACCACATCC ACAGCAACCA 20

( 2 ) INFORMATION FOR SEQ ID NO: 10:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear ( i i ) MOLECULE TYPE: synthetic or biological DNA or RNA ( x i ) SEQUENCE DESCRIPTION: SEQ ID NO:10:

AACGGCGCCG CCAGCTAGTG 20

( 2 ) INFORMATION FOR SEQ ID NO: 11:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear ( i i ) MOLECULE TYPE: synthetic or biological DNA or RNA ( x i ) SEQUENCE DESCRIPTION: SEQ ID NO:11:

TGAGCCGGAA CCTCTGCGTG 20

( 2 ) INFORMATION FOR SEQ ID NO: 12:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear ( i i ) MOLECULE TYPE: synthetic or biological DNA or RNA ( x i ) SEQUENCE DESCRIPTION: SEQ ID NO:12:

GAACACCAAC AACGCGTGCA 20

( 2 ) INFORMATION FOR SEQ ID NO: 13:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear ( i i ) MOLECULE TYPE: synthetic or biological DNA or RNA ( x i ) SEQUENCE DESCRIPTION: SEQ ID NO:13:

AGCGCCAGCT TCCGCCAGTG 20

( 2 ) INFORMATION FOR SEQ ID NO: 14:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:14:

GGTGGAGCTG CCCCAAGAGC 20

( 2 ) INFORMATION FOR SEQ ID NO: 15:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:15:

GTCCGCGCTC CCCGCGTCCA 20

( 2 ) INFORMATION FOR SEQ ID NO: 16:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:16:

GGCGCCCACG GCTCGCGCAA 20

( 2 ) INFORMATION FOR SEQ ID NO: 17:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear     ( i i ) MOLECULE TYPE: synthetic or biological DNA or RNA     ( x i ) SEQUENCE DESCRIPTION: SEQ ID NO:17:

ACAGCAACCA CCACACGGTC 20

( 2 ) INFORMATION FOR SEQ ID NO: 18:

( i ) SEQUENCE CHARACTERISTICS:
        ( A ) LENGTH: 18 base pairs
        ( B ) TYPE: nucleic acid
        ( C ) STRANDEDNESS: single stranded
        ( D ) TOPOLOGY: linear     ( x i ) SEQUENCE DESCRIPTION: SEQ ID NO:18:

TCACGGACGT GATCGACC 18

( 2 ) INFORMATION FOR SEQ ID NO: 19:

( i ) SEQUENCE CHARACTERISTICS:
 ( A ) LENGTH: 19 base pairs
 ( B ) TYPE: nucleic acid
 ( C ) STRANDEDNESS: single stranded
 ( D ) TOPOLOGY: linear ( x i ) SEQUENCE DESCRIPTION: SEQ ID NO:19:

TGTAGGTGTC GTTGGTGGT         19

( 2 ) INFORMATION FOR SEQ ID NO: 20:

( i ) SEQUENCE CHARACTERISTICS:
  ( A ) LENGTH: 180 base pairs
  ( B ) TYPE: nucleic acid
  ( C ) STRANDEDNESS: double stranded
  ( D ) TOPOLOGY: linear ( x i ) SEQUENCE DESCRIPTION: SEQ ID NO:20:

GATCACGGAC GTGATCGACC GCCGCGGCAA GTGCGTCTCC         40

AAGGCCGAGT ACGTGCGCAA CAACCACAAG GTGACCGCCT         80

TCGACCGCGA CGAGAACCCC GTCGAGGTGG ACCTGCGCCC        120

CTCGCGCCTG AACGCGCTCG GCACCCGCGG CTGGCACACC        160

ACCAACGACA CCTACACCAA        180